United States Patent

Terry

Patent Number: 5,938,674
Date of Patent: Aug. 17, 1999

[54] ASTIGMATISM REDUCING CUTTER

[76] Inventor: Clifford M. Terry, 270 Laguna Rd., Fullerton, Calif. 92835

[21] Appl. No.: 09/046,053

[22] Filed: Mar. 23, 1998

[51] Int. Cl.$^6$ .................................................. A61F 9/00
[52] U.S. Cl. ......................... 606/166; 606/161; 606/167; 606/180
[58] Field of Search ................... 606/166, 161, 606/167, 180

[56] References Cited

U.S. PATENT DOCUMENTS

| | | | |
|---|---|---|---|
| 4,423,728 | 1/1984 | Lieberman | 606/166 |
| 4,429,960 | 2/1984 | Mocilac et al. | 351/212 |
| 4,552,146 | 11/1985 | Jensen et al. | 128/305 |
| 4,665,914 | 5/1987 | Tanne | 128/305 |
| 4,744,362 | 5/1988 | Grundler | 606/166 |
| 4,750,489 | 6/1988 | Berkman et al. | 128/314 |
| 4,750,491 | 6/1988 | Kaufman et al. | 606/166 |
| 5,006,123 | 4/1991 | Soll et al. | 606/166 |
| 5,090,425 | 2/1992 | Stahl | 128/898 |
| 5,250,062 | 10/1993 | Hanna | 606/166 |
| 5,368,604 | 11/1994 | Kilmer et al. | 606/166 |
| 5,441,511 | 8/1995 | Hanna | 606/166 |
| 5,447,517 | 9/1995 | Steen et al. | 606/167 |
| 5,458,610 | 10/1995 | Feaster | 606/166 |
| 5,531,753 | 7/1996 | Oliveira | 606/166 |
| 5,545,172 | 8/1996 | Knepshield et al. | 606/166 |
| 5,591,185 | 1/1997 | Kilmer et al. | 606/161 |
| 5,618,292 | 4/1997 | Poler | 606/166 |
| 5,690,658 | 11/1997 | McAdams | 606/166 |

*Primary Examiner*—Michael Buiz
*Assistant Examiner*—(Jackie) Tan-Uyen Thi Ho
*Attorney, Agent, or Firm*—Walter A. Hackler

[57] ABSTRACT

An astigmatism reducing device includes an alignment tool having a bore, extending through said alignment tool, for enabling centering of said alignment tool by observation of a cornea limbus. A handle is provided for enabling placement of said alignment tool onto a cornea and sclera of an eye and a bottom curvature on the alignment tool engages and conforms to the cornea. A lid retractor including a channel adjacent said bottom curvature is provided for separating eyelids from said cornea and sclera and enabling a portion of the bottom curvature to be disposed thereunder. Tubular cornea cutter, having an outside diameter sized for insertion into the alignment tool bore means is provided for supporting at least one cutting blade for rotation within the alignment tool bore, the cutting blade being disposed with a longitudinal axis parallel to a longitudinal axis of the tubular cornea cutter.

22 Claims, 5 Drawing Sheets

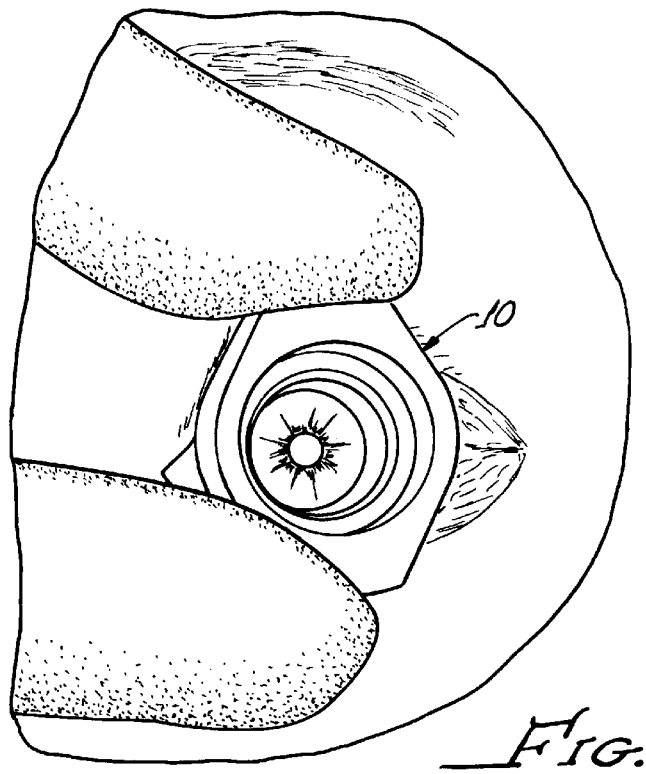
FIG. 6.
FIG. 7.
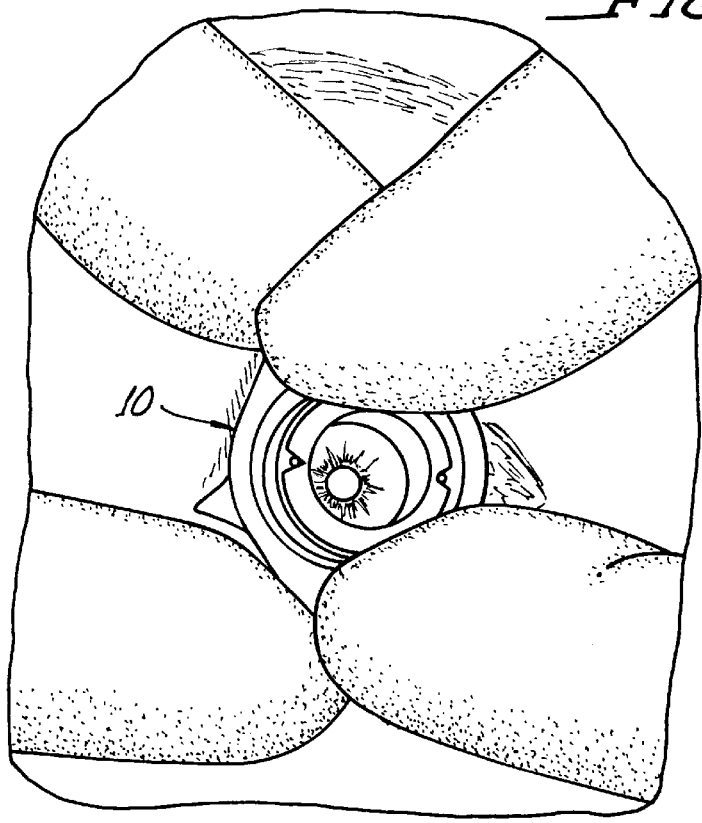

FIG. 10.
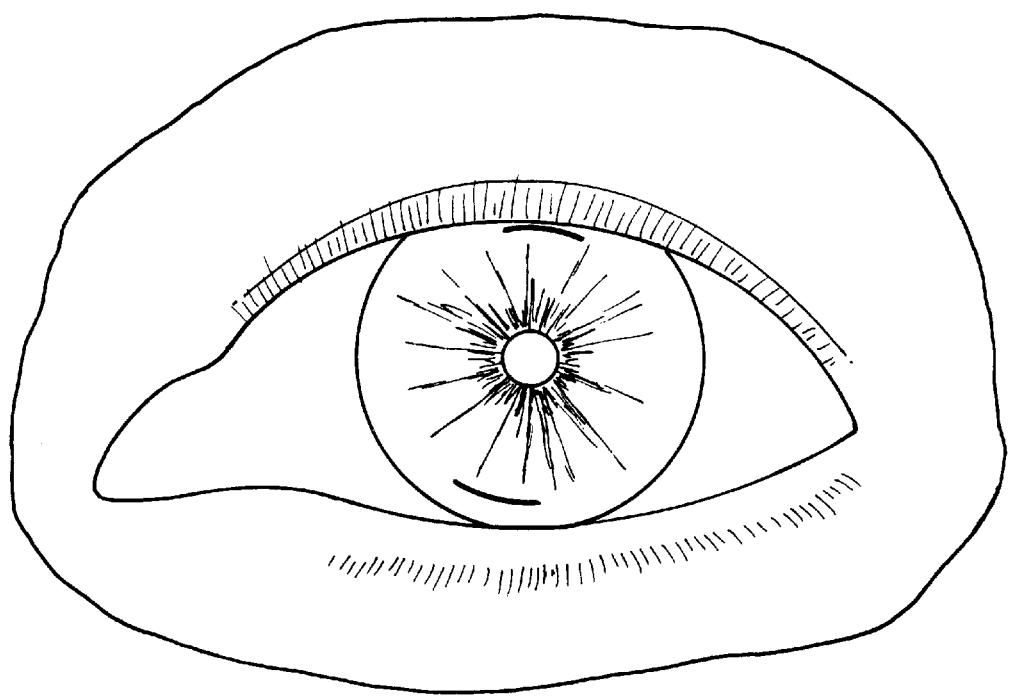
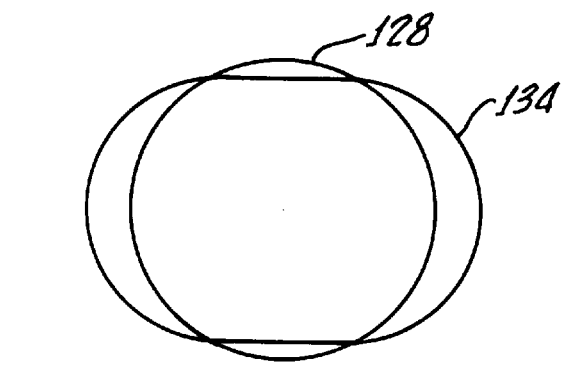
FIG. 8.
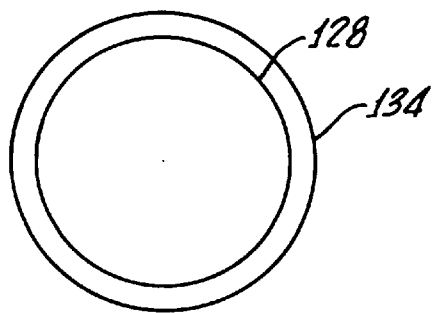
FIG. 9.

ASTIGMATISM REDUCING CUTTER

The present invention generally relates to apparatus and methods for performing ocular surgery and, more particularly, is directed to a surgical cutting device and method for placing precision cuts into a cornea to reduce corneal or refractive astigmatism.

In general, astigmatism is an ocular defect that prevents light rays from an object from meeting in a single focal point, so that indistinct images are formed. Patients are frequently born with astigmatism which, as hereinabove noted, blurs vision and necessitates the need of glasses in many cases. In addition, astigmatism may also occur after surgery of cataracts and corneal transplants. Corneal astigmatism results when a lens is not spherical in shape and in fact resembles the back surface of a spoon. In addition, astigmatism may be the result of two mutually perpendicular meridians of the anterior face of the cornea not having the same curvature.

It has been known for many years that an incision in such a cornea will flatten the curvature in the direction that it is placed. More specifically, two incisions in the cornea perpendicular to the most highly curved meridian have been utilized with the two incisions being disposed respectively on opposite sides of the optical zone.

Corneal incisions have been used for decades, for example, radial keratotomy, in which an incision is made 3 to 7 mm tangential to the pupil, usually paired on each side. Unfortunately, such incisions may cause visual aberrations and shifting of visual focus.

Arcuate incisions, for the purpose of correcting astigmatism, have been performed using a manually held blade using a circular marker to guide the surgeon. See for example, U.S. Pat. No. 5,250,062. Approximately a decade ago, surgeons developed the procedure of placing incisions at or near the zone where the clear cornea meets the white sclera, i.e., the limbus. The incisions were made by hand in the form of an arc which followed the perimeter of the limbus, with a cut being made with a scalpel where the blade tip was exposed from between about 0.5 to about 0.7 mm. Experience and empirical procedures and nomograms were utilized to determine how long the incision should be made along with an estimate of where the axis of astigmatism was located in order to place the cut symmetrically around that axis. As hereinabove pointed out, the cuts were generally paired across the cornea from each other.

Compass-like devices have been developed to make arcuate incisions in the cornea which include a device to find the center of the cornea to provide a central pivot. On this part is placed a wish-bone structure with a diamond scalpel on an arm. Unfortunately, not only is this device cumbersome, but it suffers from the need to guess the axis of astigmatism and the length and the symmetry that cuts. Worse yet, the effects of the cuts cannot be observed to titrate the effects of the incision in reducing astigmatism.

A further problem is the complexity of keeping the compass square to the cornea to get an even depth of cut. Naturally, if the blade is not tangential to the cornea, a shallow incision will result in which it reduces the effects of the incision and make a nomogram useless. On the other hand, if too much force is applied, perforation of the eye can result.

Further instruments for surgically correcting astigmatism have more recently been developed as illustrated in U.S. Pat. Nos. 5,250,062 and 5,441,511. As hereinabove noted. U.S. Pat. No. 5,250,062 is directed to a template which may be used by a surgeon for guiding a hand held surgical knife.

U.S. Pat. No. 5,441,511 is a far more complex device which includes a cone-shaped body with two diamond blades that extend from the sides. In use, a surgeon lines up the device with the center of the pupil and then attaches the device to the cornea with suction or teeth. Scales on the device for access and symmetrical rotation are provided and the diamond blades protrude through the open foot plate which buckles on the cornea upon rotation.

Unfortunately, this causes a need for cutting the incisions twice with unreliable and inconsistent cuts. Further, this device, while being very complex in construction and costly to manufacture, also lacks intra-operative measurement for precision in finding the axis of astigmatism and the effects of the cuts. Finally, the cuts are placed near the center of the eye where they may cause distortion.

Thus, there is a need for an astigmatism reducing device which can make precision cuts in the cornea of an eye without buckling thereof, while also incorporating an optical comparator for real time measurement during cutting of the cornea in order to visualize the amount of astigmatism and monitor the effects of cuts in the astigmatism reduction as the cuts are being made. This significantly reduces any guess work heretofore necessary in performing the corneal surgery to reduce the astigmatism.

SUMMARY OF THE INVENTION

An astigmatism reducing device in accordance with the present invention generally includes an alignment tool including a bore therethrough for enabling centering of the alignment tool by observation of a cornea limbus. This is distinguishable from prior art devices which utilize a central axis of the eye or pupil as an alignment reference.

A handle provides means for enabling placement of the alignment tool onto the cornea sclera of an eye and a bottom curvature on the alignment tool provides a means for engaging and conforming the alignment tool to the cornea. A lid retractor, including a channel adjacent the bottom curvature, provides means for separating eyelids from the cornea and sclera and enables a portion of the bottom curvature to be disposed thereunder.

A tubular cornea cutter, having an outside diameter sized for insertion into the alignment tool bore, provides a means for supporting at least one cutting blade for rotation within the alignment tool bore. The cutting blade may be disposed with a longitudinal axis thereof parallel to a longitudinal axis of the tubular cornea cutting means.

Importantly, the tubular cornea cutter includes a continuous circular foot blade having means defining a taper thereon for self-aligning the cutter means with a dome of the cornea. In addition, this structure applies even pressure to the cornea which enables uniform depth of cut. Because there is no space between the blade and the foot plate, buckling of the cornea does not occur. Such buckling occurs with prior art devices because they have a space between the blade and the foot plate. When the continuous circular foot plate engages the cornea, it is self-aligning on the dome of the cornea. The pressure is even, as what would be expected of a plane intercepting a dome of the cornea. During rotation, the edge of the circular foot plate causes no gathering of the cornea and pressure is exerted uniformly for a precise cut. In addition, the alignment bore and tubular cornea cutter enables real time measurement in comparison of astigmatism as the cornea is cut, as will be hereinafter described in greater detail.

Preferably, in order to eliminate any gaps between the blade and the circular foot plate of the tubular cutter, the blade is disposed along a perimeter of the cutter with a cutting edge protruding past the foot plate. In one embodiment, a second cutting may be provided and the blades may be disposed at an angular displacement of 180 degrees from one another around the cutter perimeter. In addition, the blades may be removably disposed against the cutter perimeter through the use of O-rings. Further, the blades may be angulated in order to cut the cornea at a normal to the cornea dome.

In one embodiment of the present invention, astigmatism spherometry comparator means, may be disposed within the tubular cornea cutter for enabling visual determination of the astigmatism correction during cutting of the cornea by the cutting blade.

More particularly, the astigmatism spherometer comparator means, may include a reticle window disposed within the tubular cornea cutter adjacent the footplate, and a lens disposed in a spaced apart relationship with the reticle window inside the tubular cutter. The reticle window includes an etched circular ring which provides a means for causing a reflection from the cornea when illuminated through the tubular cornea cutter. This reflection is an ellipse, and in correspondence with astigmatism.

In addition, the reticle window includes an opaque circle disposed inside of the etched circular ring which provides a means for providing a circular reference for comparison with the spherical reflection by observation through the tubular cornea cutter.

In order to facilitate arcuate cutting, the alignment tool has a top surface with a protractor scale thereon, and a tubular cutter includes indicator means, disposed in an operative relationship with a protractor scale, for displaying angular displacement between the alignment tool and the tubular cornea cutter.

A method, in accordance with the present invention for reducing astigmatism in the eye, generally includes the steps of providing an alignment tool having a bore therethrough and disposing the alignment tool against the cornea of an eye.

Centering of the alignment tool on the eye is performed by observation of the corneal limbus. A tubular cornea cutter is provided having a reticle window therein with concentric etched and opaque rings on the reticle window.

The tubular cornea cutter is inserted into the alignment tool bore, with the alignment tool against the cornea sclera. The tubular cutter is allowed to self-align with a dome of the eye pupil, and a light is directed through the radical window.

Utilizing the etched ring on the radical window and the direct light, astigmatism is determined by observing an elliptical reflection of the etched ring from the eye and comparing the elliptical reflection with the opaque ring.

Thereafter, the tubular cutter is rotated to cut the cornea and subsequent elliptical reflections are compared with the opaque ring during cutting of the cornea.

When a subsequent non-elliptical reflected image coincides with the opaque ring, the cutting of the cornea is discontinued and the alignment tool and cornea cutter are removed from the eye.

Alternatively, in accordance with the present invention, a method for reducing the astigmatism in the eye may include the steps of providing an alignment tool having a bore therethrough and disposing the alignment against the cornea of the eye.

The alignment tool is centered on the eye by observation of a cornea limbus and a provided tubular cornea cutter is inserted into the alignment tool bore with the alignment tool against the cornea and sclera.

After allowing the tubular cutter to self-align with a dome of the eye pupil, a light is directed from a provided keratometric instrument through the tubular cutter to determine the astigmatism.

The tubular cutter is then rotated to cut the cornea while observing astigmatism with the keratometric instrument. Thereafter, cutting of the cornea is discontinued when the astigmatism is reduced to a desired amount and the alignment tool and cornea cutter are removed from the eye.

BRIEF DESCRIPTION OF THE DRAWINGS

The present invention may be more clearly appreciated when taken in conjunction with the accompanying drawings, in which:

FIG. 6 is a perspective view generally showing placement of the alignment tool in an eye against the cornea sclera;

FIG. 7 is a perspective view similar to that shown in FIG. 6 illustrating the insertion of the tubular cornea cutter into a bore of the alignment tool;

FIG. 8 is a representation of a reflected etched ring as observed through the tubular cutter along with an opaque ring illustrating a degree of astigmatism;

FIG. 9 is a representation of similar to that shown in FIG. 8 illustrating corrected astigmatism; and FIG. 10 is perspective view of the eye following the cutting of the cornea with the astigmatism reducing device in accordance with the present invention.

DETAILED DESCRIPTION

Figure 1:
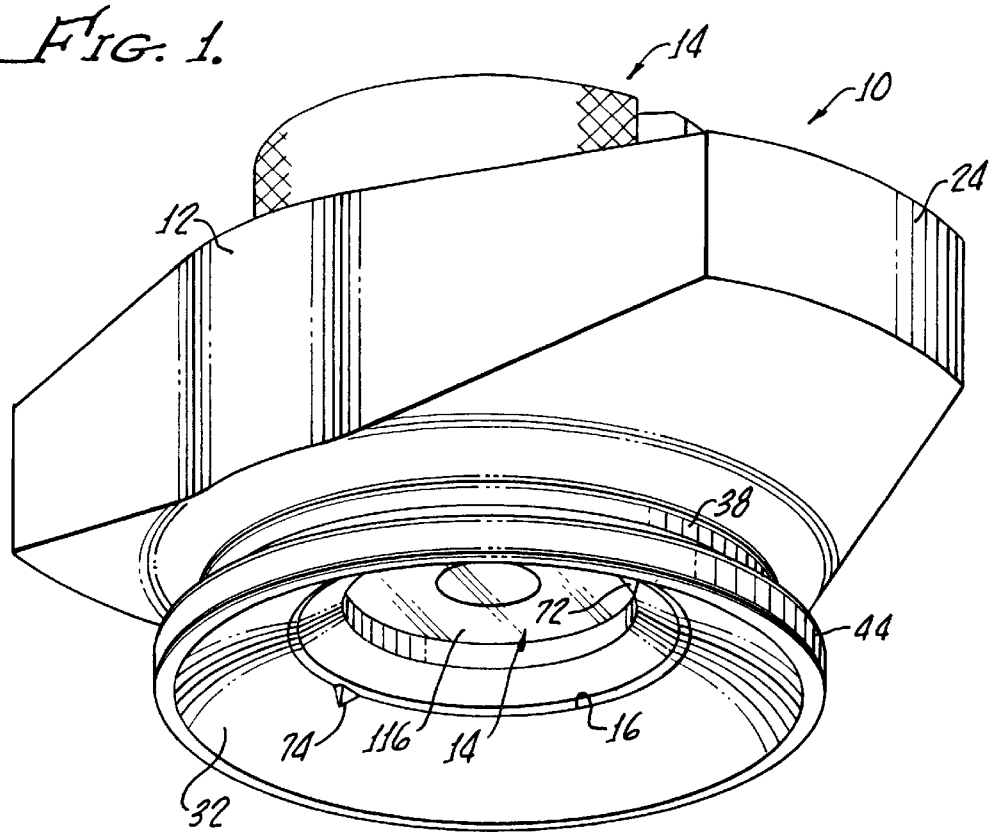
FIG. 1 is a perspective view of an astigmatism reducing device in accordance with the present invention, generally showing an alignment tool with a bore therethrough, and a tubular cornea cutter disposed therein.

Turning now to FIG. 1, there is shown an astigmatism reducing device 10 in accordance with the present invention, generally including an alignment tool 12 and a tubular cornea cutter 14 inserted into a bore 16 through the alignment tool 12. The alignment tool 12 and tubular cornea cutter 14 may be formed from any suitable material such as plastic or metal, for example, titanium.

Figure 2:
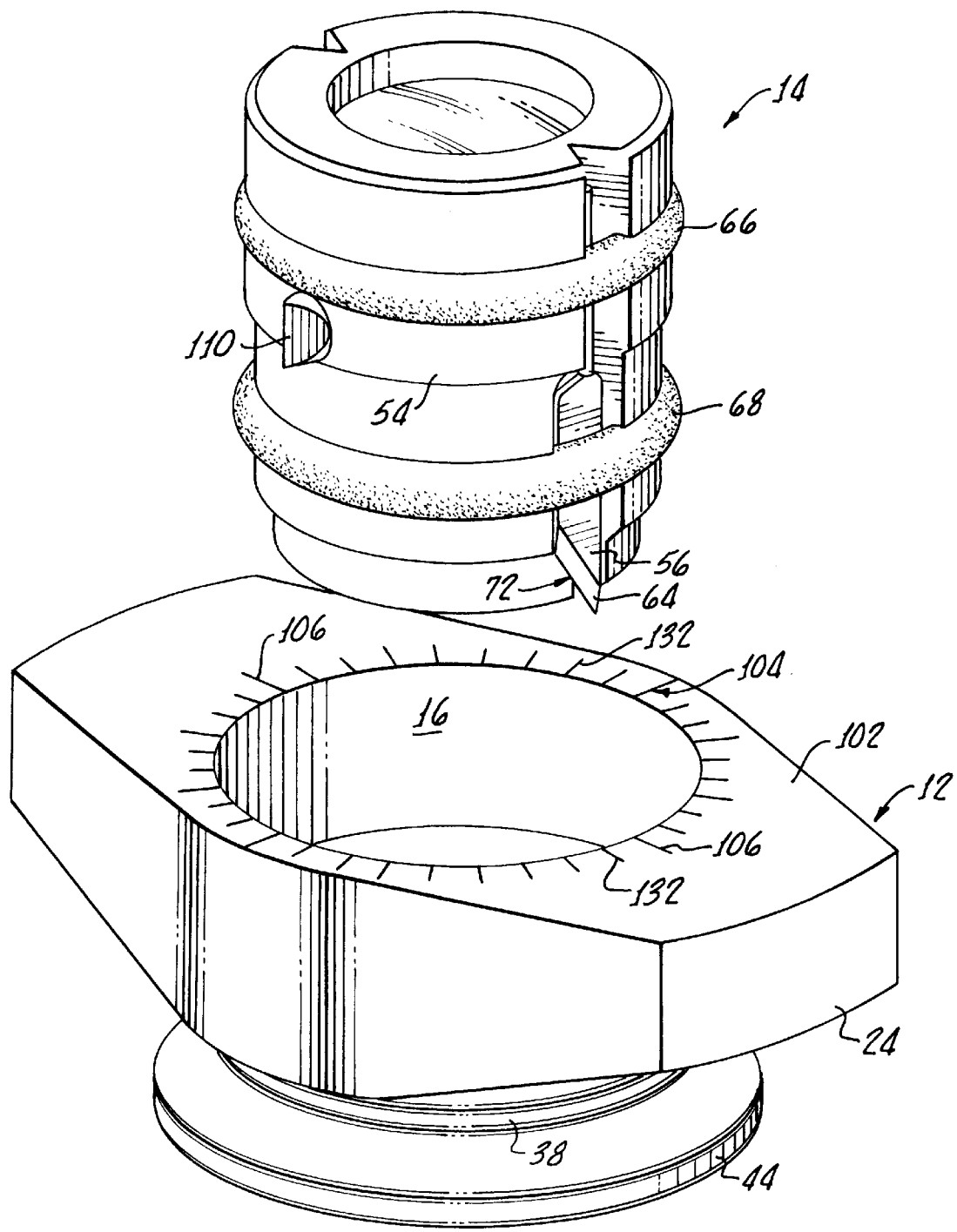
FIG. 2 is an exploded perspective view of the device shown in FIG. 1, more clearly showing a protractor disposed on the alignment tool blade disposed around a perimeter of the tubular cornea cutter and indicator means for displaying relative displacement between the tubular cornea cutter and the alignment tool.
Figure 3:
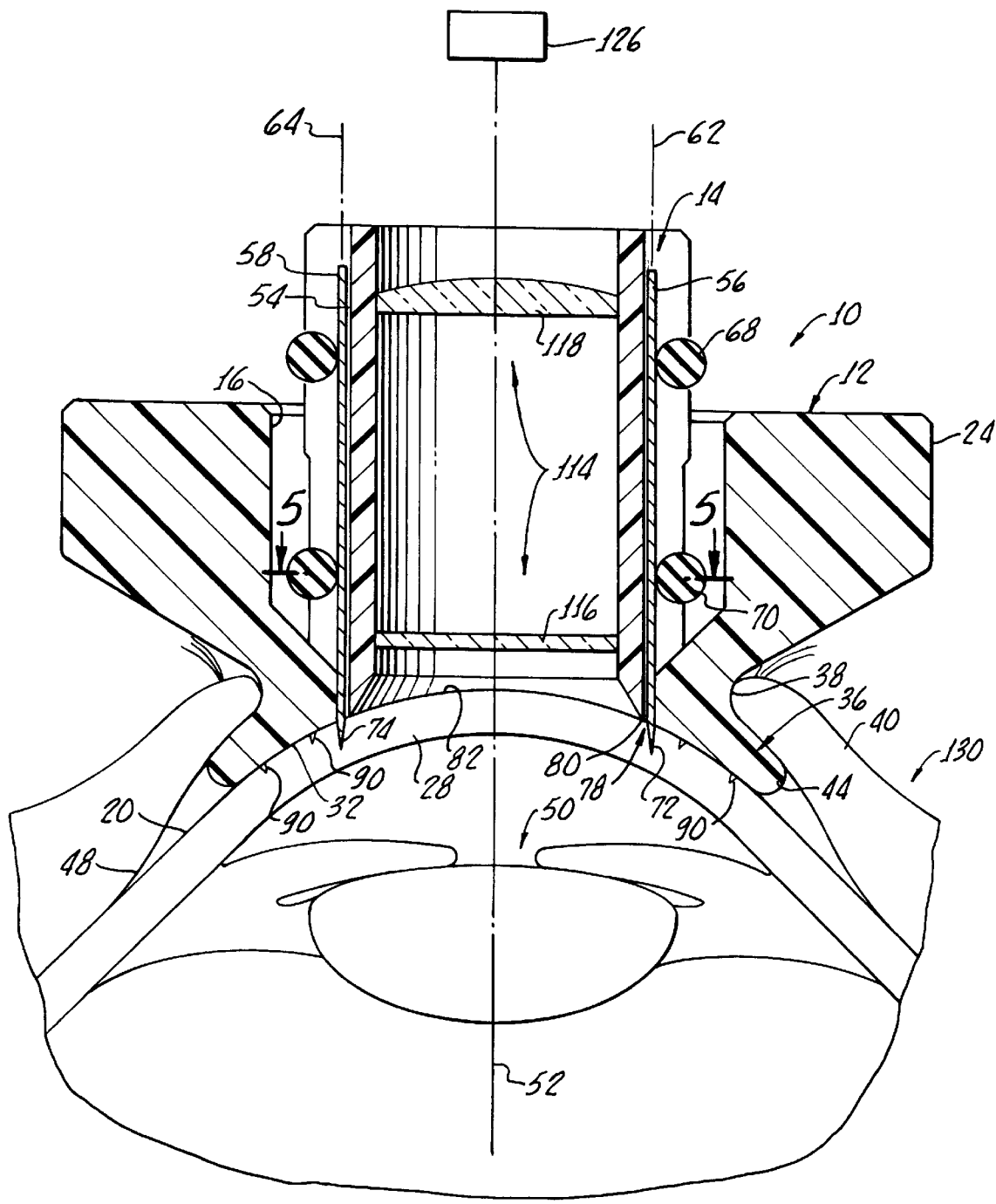
FIG. 3 is a cross section sagittal view of an eye, with the astigmatism reducing device in accordance with the present invention in contact with the cornea of an eye and properly centered for performing cuts in the cornea.

With further reference to FIGS. 2 and 3, the bore 16 through the alignment tool 12 provides a means for enabling centering of the alignment tool 12 by observance of a cornea limbus 20. The bore 16 may have an opening of about 11 to 12 mm and a finger handle 24 provides means for enabling the alignment tool 12 onto a cornea 28.

A bottom curvature 32 on the alignment tool 12 provides a means for engaging and conforming to the cornea 28 and a lid retractor 36 including a channel 38 adjacent the bottom curvature 32 provides a means for separating eye lids 40 and enabling a portion 44 of the eye lid retractor 36 to be disposed under the eye lid 40.

The alignment tool 12 is used to find the area of the cornea 28 to be cut. The opening, or bore, 16 can be moved around the cornea 12 to an orientation where the lid retractor portion 44 is completely within the clear cornea 28, but adjacent to the sclera 48. This feature and procedure is unique to all other devices since prior art devices have performed centering around the pupil or central axis 52.

The tubular cornea cutter 14 has an outside diameter 54 sized for insertion into the alignment tool bore 16 and provides a means for supporting at least one cutting blade 56 for rotation within the alignment tool bore 16.

While two cutting blades 56, 58 are shown in the figures, it should be appreciated that a single cutting blade 56 or any number of cutting blades may be utilized in accordance with the present invention. Preferably, when two cutting blades 56, 58 are utilized, they are disposed at an angular displacement of about 180 degrees from one another around the outside, or perimeter, 54 of the tubular cutter 14.

The cutting blades 56, 58 are disposed with a longitudinal axis thereof 62, 64 generally parallel to a longitudinal axis 52, which is also the visual axis. When the alignment tool 12 and tubular cutter 14 are disposed in a cutting relationship with the cornea 28 as shown in FIG. 3.

The cutting blades 56, 58 may be held against the cutter perimeter 54 by means of O-rings 68, 70 which enable longitudinal adjustment of the blades 56, 58, so that a selected cutting edge 72, 74 protrudes past a foot plate 78 on the tubular cornea cutter 14.

The circular foot plate 78 includes a taper 80 thereon which provides for self-aligning of the cutter 14 with a dome 82 of the cornea 28.

This self-centering action applies uniform and even pressure to the cornea. Importantly, no space exists between the blade edges 72, 74 and the foot plate 78 of the cornea cutter 14, hence, no buckling of the cornea occurs upon cutting of the cornea with the blades 72, 74. In addition, during rotation of the cornea cutter 14, the foot plate 78 causes no gathering of the cornea 82 and accordingly, the smooth uniform cut is established. The stability of the alignment tool 12 and the cutter 14 may be maintained by a plurality of teeth 90 for gripping the cornea 28.

Figure 4A:
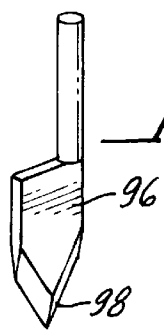
FIG. 4a is a perspective view of an alternative embodiment of a blade useful in combination with the astigmatism reducing device in accordance with the present invention showing a double cutting edge.
Figure 4B:
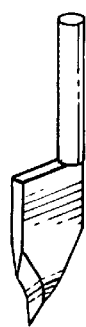
FIG. 4b is a perspective view of yet another embodiment of a blade having an angulated tip.

Each blade edge 72, 74 may be independently adjusted in its angle or protrusion from the circular foot plate 78, and each blade may be single-edged 94 as shown in FIG. 2, or alternatively as shown in FIG. 4a, a blade 96 may be double-edged 98. In addition, as shown in FIG. 4b, the blade 94, 96 may be angulated, that is, a tip portion 100 may be disposed at an angle to enable a different angle of incidence between the blade tip 100 and the cornea 18. While various angles may be utilized, an angle enabling corneal 28 incisions at a normal to the cornea dome 82 is one anticipated embodiment of the present invention.

Turning again to FIG. 2, the alignment tool 12 includes a top surface 102 having a protractor scale 104 imprinted or embossed thereon, having, for example, 36 marks 106 spaced at 10 degree increments, which may also be colored-coated. These are used as hereinafter described for proper placement of the alignment tool with respect to a steepest meridian of the cornea.

As also shown in FIG. 2, the tubular cornea cutter 14 includes an indicator 110 formed or disposed along the perimeter 54 and in an operative relationship with a protractor scale 104 to provide a means for displaying the displacement between the alignment tool 12 and the tubular cornea cutter 14. The operative relationship in this instance refers to the ability to visually observe the indicator 110 with respect to the protractor scale 104.

Importantly, the tubular cornea cutter 14 may include an astigmatism spherometry comparator 114 for enabling visual determination of the astigmatism correction during cutting of the cornea 28 by the cutting blades 56, 58.

The comparator 114 includes a reticle window 116 which may be disposed, for example, about 5 mm from the footplate 78, and a magnifying lens 118 disposed in a spaced apart relationship with the reticle window 116, both the reticle window 116 and the lens 118 being disposed within the tubular cutter 14.

Figure 5:
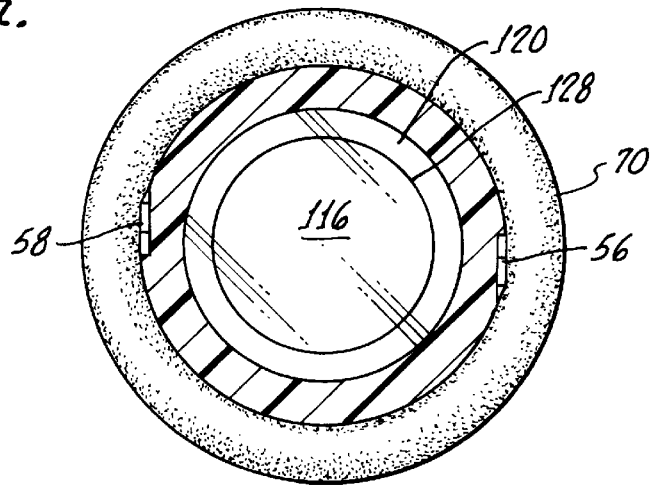
FIG. 5 is a cross sectional view of the device shown in FIG. 3 taken along the line 5—5 showing a reticle window with an etched and an opaque ring.

As shown in plan view in FIG. 5, the reticle window 116 includes an etched outer circular ring 120 which provides a means for causing a reflection from the cornea 28 when illuminated through the tubular cornea cutter 14 by a light source from, for example, an operating microscope 126. Further, an inside opaque ring 128, preferably black, provides a circular reference for comparison of the spherical reflection by observation through the tubular cornea cutter 14, as hereinafter described.

In operation, the alignment tool 12 is placed in an eye 130 which has been anesthetized. See FIG. 6. The eye lid 40 is retracted with the placement of the lid retractor 36 thereunder as shown in FIG. 3 as the finger handle 24 enables its vertical orientation over the cornea 28. The alignment tool 12 is rotated so that one of the axes as indicated by the protractor scale 104 is on the axis of the steepest degree of astigmatism. This can be achieved in three ways. One mode is to use the mires from a real time surgical keratometer for axis finding. Once the mire of the most curved meridian is found, it is centered in one of the four axes 106 of the alignment tool 12. One alternative mode is to use the comparator 114 and a third mode is to mark the lower cornea at the limbus 20 before surgery. Then the office keratometer can be used to find the axis of the plus meridian. There are 36 marks, 132, each of 10 degrees on the protractor scale 104, which can be used to align the axis. For example, if the patient has an astigmatism at 30 degrees, simply rotating the tool counterclockwise 30 degrees from the vertical cornea mark will place the tool at the steepest meridian.

In addition, the alignment tool is used to find the area of the cornea to be cut. The opening, or bore, 16 can be moved around the cornea 28 where the border is completely within the clear cornea but adjacent to the sclera 48. This procedure is unique, for as hereinabove pointed out, all prior art devices have utilized centering around the pupil or visual axis 52.

The tubular cornea cutter, or astigmatome, 14 is chosen or set to have the correct depth. The cornea 28 is measured within the conventional ultrasound device which determines thickness of the cornea and thereafter the cutting blades 56, 58 are chosen and adjusted to cut the cornea but not perforate the cornea.

The cornea cutter 14 is placed into the bore 16 of the alignment tool 12, as shown in FIG. 7, and the preliminary extension of arcs to be cut are determined. The alignment tool 12 has color coding marked at the intervals or on the axis as shown in the protractor scale 104.

An operating microscope 126 may be used to observe the cornea through the reticle window 116 and lens 118 with light from the operating microscope 126 illuminating the etched ring 120. This ring is reflected back to the observer through the tubular cutter and the degree of astigmatism is seen on the cornea as an ellipse 134 as illustrated in FIG. 8.

The tubular cutter 14 is rocked back and forth and forced slightly to penetrate the cornea and thereafter rotate it to two arcuate cuts in the cornea while observing the shape of the ellipse 130 through the lens 118 and reticle window 116. During cutting of the cornea, the ellipse 134 is transformed into a circle coinciding with the black ring 128 which provides a reference. In FIG. 9, the "ellipse" 134 is in fact a circle coinciding with the reference circle 128 and indicates that all the astigmatism has been removed. FIG. 10 is a perspective view of the eye following cutting of the cornea.

It should be appreciated that the blade 56, 58 may be bidirectional as illustrated by the blade 96 and accordingly the cuts can be symmetrically elected by extending the cut in either direction.

Importantly, the internal comparator 114 enables precision corneal alignment of the cuts which can be made of any length and done in real time while the astigmatism is visualized for more accurate results.

Alternatively, a conventional keratometer (not shown) may be utilized by observing the cornea through the tubular cutter 14 as the cornea 28 is cut. However, this requires the use of a separate and expensive device.

Although there has been hereinabove described a specific astigmatism reducing device and method in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the invention as defined in the appended claims.

What is claimed is:

1. An astigmatism reducing device comprising:
   an alignment tool including bore means, extending through said alignment tool, for enabling centering of said alignment tool by observation of a cornea limbus, handle means for enabling placement of said alignment tool onto a cornea and sclera of an eye and means, defining a bottom curvature on said alignment tool, for engaging and conforming to said cornea;
   tubular cornea cutter means, having an outside diameter sized for insertion into the alignment tool bore means, for supporting at least one cutting blade for rotation within the alignment tool bore means, the cutting blade being disposed with a longitudinal axis parallel to a longitudinal axis of said tubular cornea cutter means; and
   lid retractor means, including a channel adjacent said bottom curvature, for separating eyelids from said cornea and sclera and enabling a portion of said bottom curvature to be disposed thereunder.

2. The device according to claim 1 wherein said tubular cornea cutter means includes a continuous circular foot plate having means, defining a taper thereon, for self-aligning the cutter means with a dome of the cornea and applying even pressure thereto.

3. The device according to claim 2 wherein the blade is disposed along a perimeter of the cutter means with a cutting edge protruding past the foot plate.

4. The device according to claim 3 wherein said blade has means, defining an angulated cutting edge, for enabling corneal incisions at a normal to the cornea dome.

5. The device according to claim 3 further comprising a second cutting blade and the blades are disposed at an angular displacement of 180° from one another around the cutter means perimeter.

6. The device according to claim 5 further comprising O-ring means for removably disposing the cutting blades against the cutter means perimeter.

7. The device according to claim 1 further comprising astigmatism spherometry comparator means, disposed within said tubular cornea cutter, for enabling visual determination of astigmatism correction during cutting of the cornea by the cutting blade.

8. The device according to claim 7 wherein said astigmatism spherometry comparator means comprises a reticle window disposed within said tubular cornea cutter adjacent the foot plate and a lens disposed in a spaced apart relationship with said reticle window, said reticle window including etched circular ring means for causing a reflection from the cornea when illuminated through said tubular cornea cutter, said reflection being an ellipse and in correspondence with astigmatism.

9. The device according to claim 8 wherein said reticle window further includes opaque circle means, disposed inside said etched circular ring means on said reticle window, for providing a circular reference for comparison with the spherical reflection by observation through said tubular cornea cutter.

10. The device according to claim 1 wherein said alignment tool has a top surface with a protractor scale thereon and said tubular cornea cutter means includes indicator means, in an operative relationship with said protractor scale, for displaying angular displacement between said alignment tool and said tubular cornea cutter means.

11. An astigmatism reducing device comprising:
    an alignment tool including bore means, extending through said alignment tool, for enabling centering of said alignment tool by observation of a cornea limbus, handle means for enabling placement of said alignment tool onto a cornea and sclera of an eye and means, defining a bottom curvature on said alignment tool, for engaging and conforming to said cornea;
    tubular cornea cutter means, having an outside diameter sized for insertion into the alignment tool bore means, for supporting at least one cutting blade for rotation within the alignment tool bore means; and
    astigmatism spherometry comparator means, disposed within said tubular cornea cutter, for enabling visual determination of astigmatism correction during cutting of the cornea by the cutting blade.

12. The device according to claim 11 wherein said astigmatism spherometry comparator means comprises a reticle window and a lens disposed within said tubular cornea cutter, said reticle window and said lens being disposed in a spaced apart relationship with one another, said reticle window including etched circular ring means for causing a reflection from the cornea when illuminated through said tubular cornea cutter, said reflection being an ellipse and in correspondence with astigmatism.

13. The device according to claim 12 wherein said reticle window further includes opaque circle means, disposed inside said etched circular ring means on said reticle window, for providing a circular reference for comparison with the spherical reflection by observation through said tubular cornea cutter.

14. The device according to claim 13 wherein said alignment tool includes a protractor scale and said tubular cornea cutter means includes indicator means, in an operative relationship with said protractor scale, for displaying angular displacement between said alignment tool and said tubular cornea cutter means.

15. The device according to claim 13 wherein said tubular cornea cutter means includes a continuous circular footplate having means, defining a taper thereon, for self-aligning the cutter means with a dome of the cornea and applying even pressure thereto.

16. The device according to claim 15 wherein the blade is disposed along a perimeter of the cutter means with a cutting edge protection past the footplate.

17. The device according to claim 16 wherein said blade has means, defining an angulated cutting edge, for enabling corneal incisions at a normal to the cornea dome.

18. The device according to claim 16 further comprising a second cutting blade and the blades are disposed at an angular displacement of 180° from one another around the cutter means perimeter.

19. The device according to claim 18 further comprising O-ring means for removably disposing the cutting blades against the cutter means perimeter.

20. The device according to claim 11 further comprising lid means, including a channel adjacent said bottom retractor curvature, for separating eyelids from said cornea and sclera and enabling a portion of said bottom curvature to be disposed thereunder.

21. A method for reducing astigmatism in an eye, said method comprising the steps of:

providing an alignment tool having a bore therethrough;

disposing said alignment tool against a cornea of the eye;

centering of said alignment tool on the eye by observation of a cornea limbus;

providing a tubular cornea cutter having a reticle window therein with concentric etched and opaque rings thereon;

inserting said tubular cornea cutter into the alignment tool bore with said alignment tool against the cornea;

allowing said tubular cutter to self-align with a dome of an eye pupil;

directing a light through the reticle window;

determining astigmatism by observing an elliptical reflection of the etched ring from the eye and comparing said elliptical reflection with the opaque ring;

rotating said tubular cutter to cut said cornea;

comparing subsequent elliptical reflections with said opaque ring during cutting of said cornea;

discontinuing cutting of said cornea when a subsequent non-elliptical reflected image coincides with said opaque ring; and removing said alignment tool and cornea cutter from the eye.

22. A method for reducing astigmatism in an eye, said method comprising the steps of:

providing an alignment tool having a bore therethrough;

disposing said alignment tool against a cornea of the eye;

centering of said alignment tool on the eye by observation of a cornea limbus;

providing a tubular cornea cutter;

providing a keratometric instrument;

inserting said tubular cutter into the alignment tool bore with said alignment tool against the cornea;

allowing said tubular cutter to self-align with a dome of an eye pupil;

directing light from said keratometric instrument through said tubular cutter to determine astigmatism;

rotating said tubular cutter to cut said cornea while observing astigmatism with said keratometric instrument;

discontinuing cutting of said cornea when astigmatism is reduced to a desired amount; and removing said alignment tool and cornea cutter from the eye.

* * * * *